United States Patent [19]
Doerr

[11] Patent Number: 5,158,651
[45] Date of Patent: Oct. 27, 1992

[54] PROCESS OF CENTRIFUGALLY REMOVING INORGANIC COMPOUNDS FROM POLYESTER GLYCOL RECOVERY BOTTOMS

[75] Inventor: Marvin L. Doerr, Charlotte, N.C.

[73] Assignee: Hoechst Celanese Corporation, Somerville, N.J.

[21] Appl. No.: 536,928

[22] Filed: Jun. 11, 1990

[51] Int. Cl.$^5$ .................. B01D 3/10; B01D 45/12; C07C 29/80

[52] U.S. Cl. .................. 203/33; 203/35; 203/37; 203/38; 203/47; 203/72; 203/73; 423/76; 423/84; 568/868; 568/871

[58] Field of Search .............. 203/47, 35, 38, 33, 203/37, 48, 72, 89, 88, 73, 91, 71, 80; 568/871, 868; 423/69, 75, 87, 88, 76, 84

[56] References Cited

U.S. PATENT DOCUMENTS

| | | | |
|---|---|---|---|
| 2,788,373 | 4/1957 | Mills et al. | 568/871 |
| 3,367,847 | 2/1968 | Pierson | 568/871 |
| 4,013,519 | 3/1977 | Hoppert et al. | 568/871 |
| 4,046,688 | 9/1977 | Cunningham et al. | 423/617 |
| 4,100,253 | 7/1978 | Dougherty et al. | 423/87 |
| 4,118,582 | 10/1978 | Walker | 568/871 |
| 4,225,394 | 9/1980 | Cox et al. | 568/868 |
| 4,605,762 | 8/1986 | Mandoki | 568/871 |
| 4,808,344 | 2/1989 | Hallenburg et al. | 203/47 |

Primary Examiner—Wilbur Bascomb, Jr.
Attorney, Agent, or Firm—Philip P. McCann

[57] ABSTRACT

A process for removing inorganic compounds from glycol recovery still bottoms resulting from the manufacture of poly(ethylene terephthalate), the novel process using a small amount of phosphoric acid to precipitate the antimony and then removing the titanium dioxide and antimony compound by a centrifuge. The novel process for removing the inorganic compounds from the recovery polyester bottoms includes the steps of distilling ethylene glycol from the spent glycol until the remaining bottoms have a solids concentration from about 15% to about 45%; adding phosphoric acid to the bottoms to form an antimony compound and removing the antimony and titanium precipitates from the bottoms by a centrifuge.

15 Claims, 2 Drawing Sheets

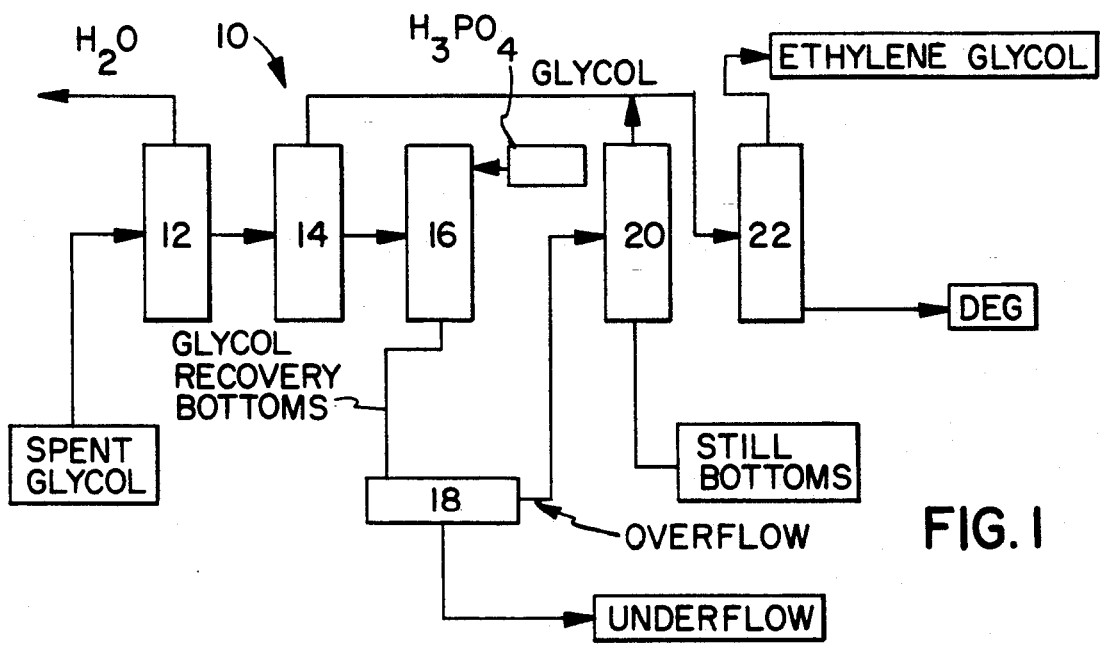
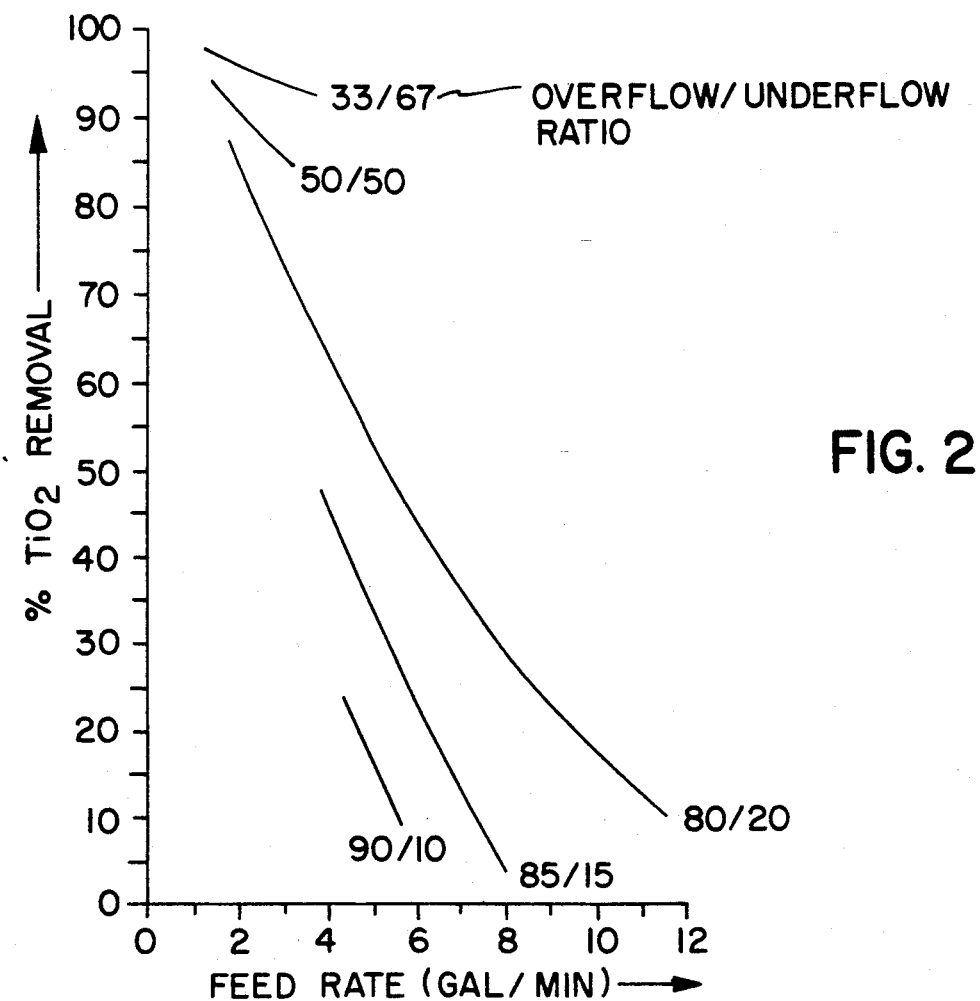

PROCESS OF CENTRIFUGALLY REMOVING INORGANIC COMPOUNDS FROM POLYESTER GLYCOL RECOVERY BOTTOMS

BACKGROUND OF THE INVENTION

1. Field of the Invention

The present invention relates to a process for removing inorganic compounds from polyester glycol recovery bottoms formed as a by-product in the manufacture of poly(ethylene terephthalate) using a centrifuge to separate the inorganic compounds from the bottoms. This process improves not only the removal of inorganic compounds, but also provides for insolubilizing inorganics, such as antimony, and then centrifugally removing the resulting antimony precipitate. In particular, the process includes forming the glycol recovery bottoms by distilling spent glycol produced as a by-product of polyester to have a solids concentration from about 15% to about 45%, and centrifuging the glycol recovery bottoms to remove the inorganic compounds. In addition to the centrifugal removal of inorganic compounds, the addition of a precipitating reagent to the glycol recovery bottoms before the centrifuging of the glycol recovery bottoms insolubilizes other inorganic compounds which can also be centrifugally removed. In particular, it has been found that adding a mole ratio of about 2 P/Sb as phosphoric acid before centrifuging permits the removal of antimony and increases the amount of removal of $TiO_2$.

2. Prior Art

Poly(ethylene terephthalate) (PET) is a commercial film and fiber forming polyester which is generally manufactured by reacting a lower dialkyl ester of a dicarboxylic acid such as dimethyl terephthalate (DMT) with a molar excess of ethylene glycol (EG) in the presence of a catalyst (such as compounds of manganese, zinc, calcium, magnesium, for example). A delustrant such as $TiO_2$ is also added. These components undergo ester interchange to yield bishydroxyethyl terephthalate (BHET) and methanol. Phosphorus is preferably added to sequester the ester interchange catalyst. Alternatively, BHET may be produced by the direct esterification of terephthalic acid (TA) also with an excess of ethylene glycol (EG). The BHET is then polymerized by a polycondensation reaction in the presence of a suitable polymerization catalyst (such as an antimony compound). From this reaction PET and spent ethylene glycol are formed. Because the polycondensation reaction is reversible, the excess spent glycol is removed as it is evolved, thus forcing the reaction toward the formation of the polyester. Large quantities of spent ethylene glycol distillate, hereinafter "spent glycol", are produced during the polymerization reaction.

Unfortunately, the spent glycol contains impurities which make it unsuitable, as is, for the manufacture of PET or for other uses such as the production of polyols, polyurethane foams, and unsaturated polyester resins, etc. For instance, a typical spent glycol contains mostly ethylene glycol, along with various quantities of diethylene glycol, water, polyester oligomers, and inorganic compounds. Contained in the inorganic organic compounds are titanium dioxide, phosphorus and about 50 to 500 ppm of antimony. Accordingly, it is standard practice in the industry to purify the spent glycol, recovering distilled glycol and reusing the recovered glycol in the manufacture of PET. A by-product of this purification is a mass known in the industry as polyester glycol recovery bottoms, in which is contained inorganic compounds. The inorganics are concentrated 30 to 50 times in the bottoms by the ethylene glycol recovery process. The presence of some inorganic compounds such as antimony compounds or titanium dioxide makes the by-product unusable. Removal of these inorganic compounds has proved troublesome to date.

In prior art processes, the spent glycol is passed through a light-ends removal column (water stripper column) under reduced pressure and at a column top temperature of about 75° C. The glycol is then fractionally distilled in one or more columns or in flash or thin-film evaporators under vacuum condition, ranging from about 20 to 200 mm mercury absolute pressure and at a temperature of from about 130°-160° C. The glycols including ethylene and diethylene glycol are recovered from the spent glycol as a overhead stream. The glycols are further distilled to separate the ethylene glycol from the diethylene glycol. In a typical distillation about 90 to 95% of the ethylene glycol present in the spent glycol is recovered in the overhead stream, the balance remaining in the bottoms and dehydrated to diethylene glycol.

As the glycols are fractionally distilled, most of the residual impurities remain in the bottom of the column or the evaporator taking the form of a waxy granulated mass and will be referenced to as "glycol recovery bottoms or bottoms". A typical bottom includes about 98% terephthalate esters and glycols (ethylene and diethylene) and about 2% of inorganic compounds of Sb and P including $TiO_2$.

The terephthalate ester and diethylene glycol of the polyester bottoms are known to have commercial applications in markets including polyol/polyurethane and unsaturated polyester resin which use crude terephthalate streams as raw materials. However, specifically the inorganic compounds of Sb and $TiO_2$, have been found intolerable in such applications. No known problem has ever been associated to date with phosphorus in downstream end uses. Without such commercial applications, polyester glycol recovery bottoms containing these inorganic compounds require disposal by burying or incinerating. However, antimony is known to be highly toxic. The Environmental Protection Agency (EPA) has taken the position that the presence of antimony constitutes an environmental and subsequent health hazard. A maximum acceptable limit of 5 PPM of antimony has been established by the EPA for effluent discharged into a waterway. A problem with incinerating polyester bottoms is the high volatility of antimony oxides. Pretreating for burying or incinerating to mitigate antimony-related problems becomes enormously expensive.

The following references are directed to various methods for purifying spent glycol and methods of separating the inorganic impurities from the glycol recovery bottoms.

U.S. Pat. No. 2,788,373 to Mills, Jr. et al discloses a process for recovering ethylene glycol from spent glycol using an acid to precipitate out soluble solid matter. In particular, the spent glycol is first diluted with water and a mineral acid such as phosphoric acid is added to precipitate out soluble solid matter usually terephthalate salts. The precipitated solid matter is removed by decantation or filtration.

U.S. Pat. No. 4,013,519 to Hoppert et al discloses recovering antimony from the polyester bottoms by alkaline hydrolysis, acidification and filtration to remove antimony sulfide precipitate from spent glycol. Such a process is disclosed to remove terephthalic acid from the polyester bottoms without contamination by the antimony. The uncontaminated terephthalic acid can be recycled for polyester manufacture or other use.

U.S. Pat. No. 4,046,688 to Cunningham et al discloses a process to recover dissolved antimony using a strong acid and/or a strong base in an ion exchange resin to absorb the antimony. This process is done after the spent glycol has been filtered to remove suspended solids.

U.S. Pat. No. 4,100,253 to Dougherty et al discloses a process to recover antimony from spent glycol by incineration. In particular, the polyester bottoms are incinerated to produce an ash and then the ash is contacted with water to form an ash-water from which the antimony compounds can be recovered.

U.S. Pat. No. 4,118,582 to Walker discloses a process to recover antimony from spent glycol by precipitating out the antimony with an alkali metal borohydride. The process can be enhanced by adding a strong inorganic base.

Improvements which remove just antimony but not titanium dioxide, for example, partially solves the foregoing problem. However, one goal of the present invention is to remove both the antimony and titanium dioxide.

There remains a need to develop a process for the purification of polyester glycol recovery bottoms which minimizes the problems of disposal of the polyester bottoms so the polyester bottoms can be recycled for other uses. Especially desired is an improved process wherein contaminates present in glycol recovery bottoms, such as antimony and titanium dioxide can be economically removed.

SUMMARY OF THE INVENTION

The present invention provides a process which is effective and economical in purifying polyester glycol recovery bottoms by separating out solid inorganic precipitates from the bottoms using a centrifuge. Furthermore, the present invention may also combine a precipitating agent in the glycol recovery bottoms and uses the precipitating agent in specific amounts and under a unique manner so as to insolubilize inorganics such as antimony for precipitation as well as improve the removal of other inorganic compounds. In particular, the present invention comprises distilling the spent glycol to form polyester glycol recovery bottoms having a specific solids concentration, then centrifuging the glycol recovery bottoms to remove the inorganic compounds. A precipitating agent such as phosphoric acid can be added to the glycol recovery bottoms before centrifuging to form an inorganic precipitate that can be removed by centrifuging.

Furthermore, the present invention provides a process for removing inorganic compounds from polyester glycol recovery bottoms which include, in addition to the inorganic compounds, polyester materials, terephthalate esters and glycols. The polyester glycol bottoms are formed in the recovery of spent glycol produced as a by-product in the manufacture of polyester to which inorganic compounds are added, wherein the spent glycol contains glycol, terephthalate esters and the inorganic compounds, and the spent glycol has a solids concentration of less than about 5%. The improvement of the present invention comprises the steps of: distilling the spent glycol to form the glycol recovery bottoms such that the glycol recovery bottoms having a solids concentration from 15% to about 45%; and centrifuging the glycol recovery bottoms to remove the inorganic compounds.

The foregoing process can be further enhanced by adding a precipitating reagent to the glycol recovery bottoms before centrifuging to precipitate inorganics such as antimony which is then removed by centrifuging. In particular, a preferred precipitating agent is phosphoric acid, the mole ratio of the phosphorus of the phosphoric acid to antimony is from about 1.0 to about 3.0.

BRIEF DESCRIPTION OF THE DRAWING

FIG. 1 depicts a flow sheet of a specific embodiment of the process of this invention.

FIG. 2 shows various graphs illustrating the relationship of $TiO_2$ removal and feed rate.

DESCRIPTION OF THE PREFERRED EMBODIMENTS

Figure 4:
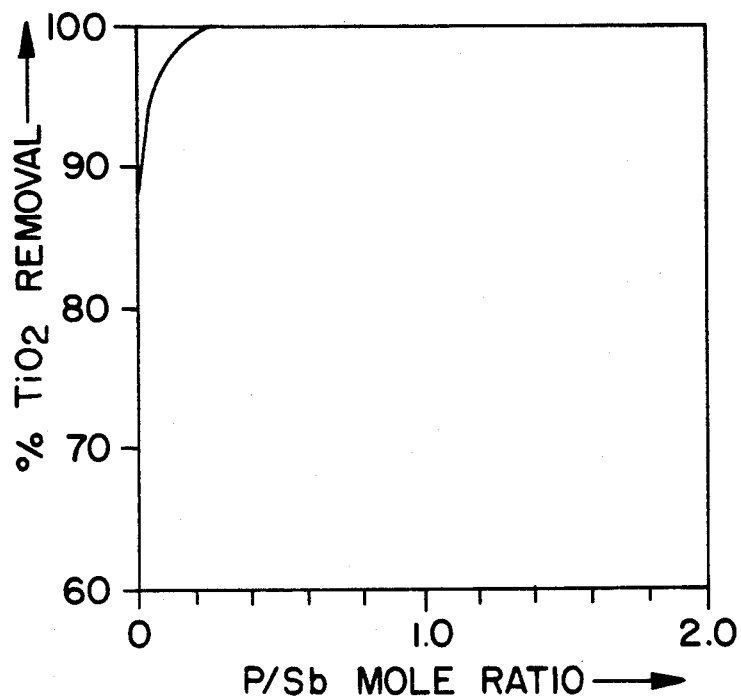
FIG. 4 shows a graph illustrating the relationship of $TiO_2$ removal and the mole ratio of phosphorus to antimony.

A typical spent glycol formed as a by-product in a commercial poly(ethylene terephthalate) manufacturing plant contains about 70 to 97% ethylene glycol, about 0.5 to 1% diethylene glycol, up to 3% terephthalate oligomers, up to 25% water, and inorganic compounds including about 50–500 ppm antimony, in the form of dissolved organic antimony compounds, up to 200 ppm titanium in the form of titanium dioxide ($TiO_2$), and up to about 200 ppm phosphorus in the form of phosphorous or phosphoric acid or their organic esters, and trace quantities of other contaminants. Distillation procedures, such as fractional and flash distillation, are conventionally used to remove water and other low-boiling materials from the spent glycol and recover most of the ethylene glycol present in the spent glycol.

In accordance with the present invention, inorganic compounds present in the glycol are rendered insoluble, if required, and then centrifugally removed after the spent glycol has been distilled to form glycol recovery bottoms having a solids concentration from about 15% to about 45% to allow for the efficiency of centrifuging during the removal of the inorganic compounds.

The spent glycol is first passed through a light-end distillation column where all low-boiling components are removed, including water which may be present in amounts up to about 25%. This column generally operates under a vacuum of about 250 mm mercury absolute pressure with column top temperature of about 75° C.

After the water and other low-boiling materials have been removed from the spent glycol, the spent glycol is transferred to a second distillation column or an evaporator wherein the spent glycol is distilled at a vacuum of about 175 mm mercury absolute pressure and a temperature from about 130° C. to about 150° C. to remove a certain portion of ethylene glycol such that the residual product referenced herein as glycol recovery bottoms has a solids concentration from about 15% to about 45%. Within the specified solids concentration range, the resulting glycol recovery bottoms contains ethylene glycol, diethylene glycol, and solids including the terephthalate oligomers and the inorganic compounds.

The glycol recovery bottoms are then transferred to a storage tank and a precipitating reagent is added under controlled conditions. This reagent is added when inorganic elements such as antimony require insolubilization. Suitable precipitating reagents include trimethyl phosphite, tridecyl phosphite, sodium bisulfite, sodium hydroxide and phosphoric acid. Phosphoric acid is the preferred precipitating reagent. The precipitating agent is generally added to the hot glycol recovery bottoms in the storage tank.

Intimate mixing of the glycol recovery bottoms and precipitating reagent is important, both as they are brought together and during the course of the reaction. Reaction efficiency suffers unless there is intimate mixing of the components. For that reason, the spent glycol is continuously agitated during the course of mixing the precipitating agent with the spent glycol.

The chemical equation for the reaction of trivalent antimony with phosphoric acid is

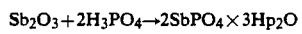

$$Sb_2O_3 + 2H_3PO_4 \rightarrow 2SbPO_4 \times 3H_pO$$

Figure 3:
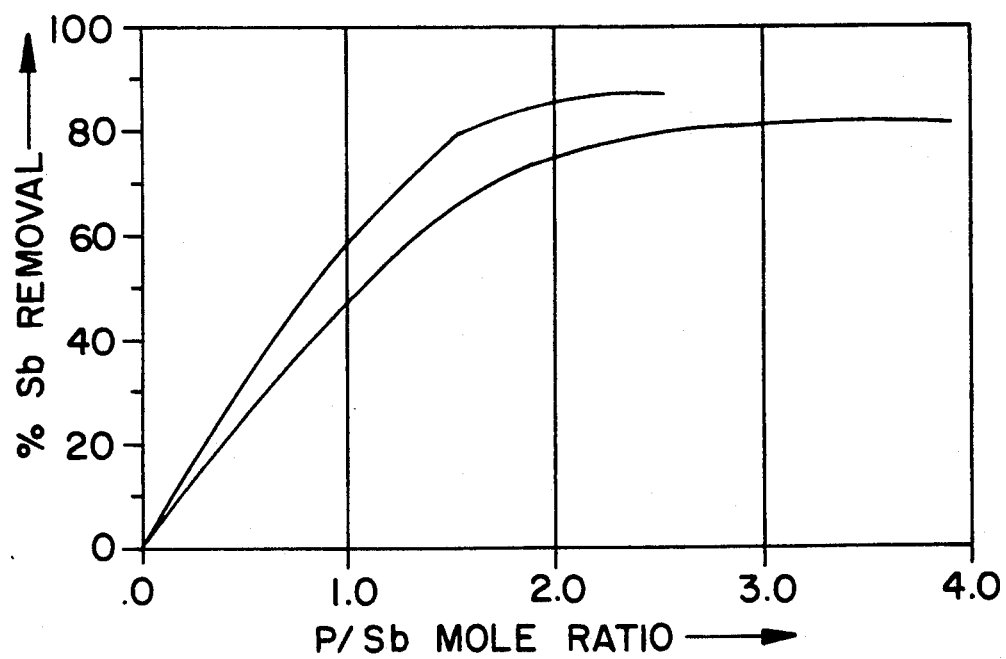
FIG. 3 shows a graph illustrating the relationship of antimony removal and the mole ratio of phosphorus to antimony.

By stoichiometric principles, one mole of phosphorus will react with on mole of antimony. Under the prescribed ratio of 1:1 of P to Sb, about 50% of the dissolved antimony compound can be precipitated as antimony phosphate. When the mole ratio of P to Sb was increased to about 2:1, up to 90% or more of the dissolved antimony compounds can be precipitated. FIG. 3 illustrates the relationship of the percent antimony removal to the mole ratio of P/Sb. As shown by the graphs, the antimony removal percentage levels off dramatically when the mole ratio exceeds 2:1. The data basis for the graph is contained in the subsequent Example 3.

The glycol recovery bottoms containing the precipitated antimony in addition to the other inorganic compounds is then fed into a centrifuge for the removal of the inorganic precipitates. In particular, the present invention is preferably directed to the removal of titanium dioxide and/or the antimony precipitate. Each of these inorganic contaminates can be removed individually or in combination. By processing through the centrifuge, the inorganic contaminates are concentrated in an "underflow" which is then collected.

Centrifuges suitable for use in the present invention generally have feed rates dependent on the centrifuge capacity, are rotatable at rpm from 3000 to 6600 rpm and have a variable overflow/underflow ratio, generally from about 80/20 to about 95/5 being preferred. All centrifuge processes result in an "underflow" or a "cake" or a cut of material which is being centrifuged out as unwanted material. The size or fraction of the underflow is controllable, but is found to be dependent of the centrifuging efficiency of the overflow or the mainstream.

Reduction of underflow to as low as possible is desirable. Some centrifuges are designed to recirculate the underflow to further remove the insolubles. Increase in the overflow/underflow ratio directly affect the amount of contaminant removed. For example, in the case of removing only precipitates such as $TiO_2$ from the spent glycol, it was found that for an overflow/underflow ratio of 33/67, 98% removal of the $TiO_2$ could be attained at a feed rate of 1.5 gal/min. For an overflow/underflow ratio of 50/50, 89% removal rate would occur at 2 gal/min. For an overflow/underflow ratio of 80/20, a 53% removal could be attained at a feed rate of 5 gal/min, a 31% removal at a feed rate of 7.5 gal/min and only a 15% removal at a feed rate of 10 gal/min. For an overflow/underflow ratio of 90/10, only 14% removal rate could be attained at a feed rate of 5 gal/min. In view of the dependency of the removal rate and flow rate, the ratio of overflow/underflow is dependent on the processing rate and the economics of removing the inorganic compounds versus disposal of the underflow.

In the case when phosphoric acid is added to precipitate the antimony, it was surprisingly found the percentage of $TiO_2$ removal increased. In particular, it was found that in excess of 99% $TiO_2$ removal was achieved when a molar ratio of P/Sb was about 2:1 and the centrifuge was operated at about 2.45 gal/min. and an overflow/underflow of about 80/20. Without the phosphoric acid, only about 75% of the $TiO_2$ was removed as shown in FIG. 2.

The centrifuged precipitate can be further processed to recover usable materials. For example, the recovered antimony can be oxidized, in a furnace, for instance, to convert it to antimony oxide. The claimed antimony oxide may be recycled for reuse. Incineration also allows for the recovery of the $TiO_2$ which remains in the ash product.

After centrifuge treatment of the glycol recovery bottoms to remove the inorganic contaminants, the overflow is further distilled to recover as much ethylene glycol as is possible for the manufacture of PET. The deposit of still bottoms contains the remaining impurities including terephthalate esters and glycols. The still bottoms absent the inorganic contaminant are of commercial value and can be sold to the polyol/polyurethane industry and the unsaturated polyester resin industry.

EXPERIMENTAL PROCEDURE

A specific embodiment of the process of the present invention is depicted by 10 in FIG. 1 and may be generally performed as follows:

Spent glycol taken from the manufacture of poly-(ethylene terephthalate) containing by weight about 76% ethylene glycol, 0.7% diethylene glycol, 2.0% oligomers, 20.3% water and 1% inorganic compounds including antimony, titanium and phosphorus compounds was fed into a distillation column 12 wherein the water and other low-boiling impurities are removed from the spent glycol. Feed rate into the column was about 25 gal/min. Removal occurred at a head temperature of about 75° C. and under a vacuum at about 250 mm mercury absolute pressure.

The spent glycol was then fed into a flash evaporator 14 wherein glycol is removed at a head temperature of about 140° C. and under a vacuum of about 175 mm mercury absolute pressure such that the remaining glycol recovery bottoms reaches a solids concentration between about 15 and 45%. The glycol recovery bottoms are then transferred to an atmospheric storage tank 16 wherein phosphoric acid is added to the glycol recovery bottoms. The tank 16 is heated to about 140° C. and continuously agitated.

From the storage tank, the glycol recovery bottoms are fed into a Dorr-Oliver Model PC-9 centrifuge 18 wherein the insoluble inorganic compounds are separated from the glycol recovery bottoms. Testing of the glycol bottoms for remaining inorganic compounds can be performed at this point. Subsequent to the centrifuging, the centrifuge overflow is fed into a thin-film evaporator 20 wherein additional glycols are separated from the bottoms. The glycol streams from both evaporators are sent to a fractionating column 22 operated under reduced pressure where the purified ethylene glycol is taken off as overhead stream and diethylene glycol is taken off as a side stream.

EXAMPLE 1

Various centrifuge parameters were employed to demonstrate the present invention for removal of the inorganic contaminant titanium dioxide. Throughout the 9 experiments, the glycol recovery bottoms fed from the storage tank to the centrifuge contained from about 64% to about 72% ethylene glycol, 5% diethylene glycol, solids as designated which include the inorganic contaminants.

Experiment 1 employs an overflow/underflow ratio of 90/10, a flow rate of 5 gal/min and a solids concentration of the spent glycol of about 22%.

Experiments 2 and 3 were similar to Experiment 1 except the overflow/underflow ratio was held at 85/15 and the solids concentration was 27% and the flow rate was varied.

In Experiments 4-6, the solids concentration was about 23% and the overflow/underflow ratio was about 80/20 while the flow rates varied from 10 to 5 gal/min.

Experiments 7 was similar to Experiment 1 except the overflow/underflow ratio was 75/25, flow rate was 3.6 gal/min.

Similarly, Experiments 8 and 9 varied all three parameters.

From these results, it is clear that phosphoric acid outperformed the other precipitating reagents.

EXAMPLE 3

Various mole ratios of phosphorus to antimony were employed to demonstrate the preferred ratio. In Experiments 1 and 5 (controls), no phosphoric acid was added to a antimony-containing glycol slurry. Experiments 2 and 6 used a mole ratio of about 0.8, Experiments 3 and 7 about 1.6, Experiments 4 and 8, 2.35 and 2.6 respectively and Experiment 9 a mole ratio of 3.85.

TABLE III

| | Experiment | | | | | | | | |
|---|---|---|---|---|---|---|---|---|---|
| | 1 | 2 | 3 | 4 | 5 | 6 | 7 | 8 | 9 |
| P/Sb mole ratio | 0 | 0.77 | 1.56 | 2.35 | 0 | 0.76 | 1.60 | 2.60 | 3.85 |
| % Sb Removal | 0 | 43 | 82 | 87 | 0 | 35 | 68 | 79 | 81 |

The results of Example 3 are shown in FIG. 3. The graphs clearly show that antimony removal continues to increase beyond the stoichiometric ratio of 1:1 up to about 2:1 where the removal rate dramatically levels off.

EXAMPLE 4

Various levels of phosphoric acid were employed to demonstrate the unexpected synergism created by adding the phosphoric acid to remove both the titanium and antimony. In these experiments, phosphoric acid was added to the spent glycol prior to the centrifuge. The glycol was fed at 2.45 gal/min into a centrifuge having a overflow/underflow ratio of 80/20 and operating at

TABLE I

| | 1 | 2 | 3 | 4 | 5 | 6 | 7 | 8 | 9 |
|---|---|---|---|---|---|---|---|---|---|
| % Solids Concentration | 22 | 27 | 27 | 23 | 23 | 23 | 22 | 22 | 30 |
| Overflow/underflow | 90/10 | 85/15 | 85/15 | 80/20 | 80/20 | 80/20 | 75/25 | 50/50 | 33/67 |
| Flow Rate (gal/min) | 5.0 | 8.0 | 5.5 | 10 | 7.5 | 5.0 | 3.6 | 2.0 | 1.5 |
| $TiO_2$ In Feed (ppm) | 4150 | 3640 | 3640 | 4000 | 4000 | 4000 | 4150 | 4150 | 4160 |
| Overflow (ppm) | 3570 | 3590 | 2720 | 3420 | 2770 | 1900 | 2190 | 440 | 90 |
| % Removal | 14 | 1 | 25 | 15 | 31 | 53 | 47 | 89 | 98 |

The % $TiO_2$ removal using the centrifuge is shown in FIG. 2. Clearly shown are the highest rates of removal of $TiO_2$ are attained at low overflow/underflow ratios, low flow rates and solids concentration of about 30%.

EXAMPLE 2

Various precipitating reagents were employed to demonstrate those suitable for precipitating out antimony from a glycol slurry. To a solution of glycol-solubilized antimony containing about 200 ppm Sb, is added at 90° C. an excess of each reagent listed in Table II.

TABLE II

| Precipitating Reagent | % Sb Removal |
|---|---|
| Trimethyl Phosphite | 71 |
| Tridecyl Phosphite | 76 |
| Sodium Bisulfite | 79 |
| Sodium Hydroxide | 89 |
| Phosphoric Acid | 92-98% |

4800 rpm.

Experiments 1, 2 and 3 contained only trace amounts of phosphoric acid while experiments 4 and 5 contained more than 2 mole ratio of P/Sb.

TABLE IV

| | Experiment | | | | |
|---|---|---|---|---|---|
| | 1 | 2 | 3 | 4 | 5 |
| P/Sb Ratio | 0.1 | 0.1 | 0.2 | >2.0 | >2.0 |
| % $TiO_2$ Removal | 97.5 | 94 | 99.7 | 100 | 99.2 |
| % Sb Removal | 6 | 11 | 18 | 85 | 98.4 |

Surprisingly, in experiments 4 and 5 the removal rates of the $TiO_2$ increased to nearly 100% while the % Sb removal remained good. These results were illustrated in FIG. 4.

Thus, it is apparent that there has been provided in accordance with the invention, a method of removing inorganic contaminants from recovery polyester bottoms using a centrifuge that fully satisfies the objects, aims and advantages as set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations that fall within the sphere and scope of the invention.

That which is claimed is:

1. A process for producing recyclable polyester glycol recovery bottoms by removing inorganic compounds from polyester glycol recovery bottoms which include, in addition to the inorganic compounds, polyester materials, terephthalate esters and glycols, said polyester glycol recovery bottoms formed in the recovery of spent glycol produced in the manufacture of polyester to which inorganic compounds are added, wherein the spent glycol contains glycol, terephthalate esters and inorganic compounds, said spent glycol having a solids concentration of less than 5%, the improvement consisting essentially of the steps;

distilling the spent glycol to obtain, as a bottoms product, the polyester glycol recovery bottoms such that the polyester glycol recovery bottoms have a solids concentration from about 15% to about 45%, and centrifuging said glycol recovery bottoms with a centrifuge to remove the inorganic compounds leaving recyclable polyester glycol recovery bottoms.

2. The process of claim 1, wherein said inorganic compounds include titanium dioxide.

3. The process of claim 1, wherein the spent glycol is distilled to obtain, as a bottoms product, the polyester glycol recovery bottoms such that the polyester glycol recovery bottoms have a solids concentration from about 20 to about 35%.

4. The process of claim 1, wherein the polyester glycol recovery bottoms flow into the centrifuge at a flow rate from about 1 gal/min. to about 20 gal/min.

5. The process of claim 4, wherein the centrifuge has an overflow/underflow ratio from about 33/67 to about 95/5.

6. The process of claim 4 wherein the centrifuge has an overflow/underflow ratio from about 80/20 to about 95/5.

7. A process for producing recyclable polyester glycol recovery bottoms by removing inorganic compounds from polyester glycol recovery bottoms which include, in addition to the inorganic compounds, polyester materials, terephthalate esters and glycols, said polyester glycol recovery bottoms formed in the recovery of spent glycol produced in the manufacture of polyester to which inorganic compounds are added, wherein the spent glycol contains glycol, terephthalate esters and inorganic compounds, said spent glycol having a solids concentration of less than 5%, the improvement consisting essentially of the steps:

a) distilling the spent glycol to obtain, as a bottoms product, the polyester glycol recovery bottoms such that the polyester glycol recovery bottoms have a solids concentration from about 15% to about 45%;

b) adding a precipitating reagent to the glycol recovery bottoms in sufficient quantity to precipitate out any solubilized inorganic compounds; and c) centrifuging said glycol recovery bottoms with a centrifuge to remove the inorganic compounds leaving recyclable polyester glycol recyclable bottoms.

8. The process of claim 7 wherein said inorganic compounds include antimony compounds.

9. The process of claim 8 wherein said precipitating agent is selected from the group consisting essentially of trimethyl phosphite, tridecyl phosphite, sodium bisulfite, sodium hydroxide and phosphoric acid.

10. The process of claim 8 wherein said precipitating agent is phosphoric acid.

11. The process of claim 7 wherein said inorganic compounds include antimony compounds and titanium dioxide and said precipitating agent is phosphoric acid.

12. The process of claim 11 wherein the spent glycol is distilled to obtain, as a bottoms product, the polyester glycol recovery bottoms such that the polyester glycol recovery bottoms have a solids concentration from about 20 to about 35%.

13. The process of claim 11 wherein the centrifuging is accomplished with a centrifuge and the glycol recovery bottoms are fed into the centrifuge at a flow rate from about 1 gal/min to about 20 gal/min.

14. The process of claim 13 wherein the centrifuge has an overflow/underflow ratio from about 33/67 to about 95/5.

15. The process of claim 13 wherein the centrifuge has an overflow/underflow ratio from about 80/20 to about 95/5.

* * * * *